(12) United States Patent
Nishiyama

(10) Patent No.: US 9,109,986 B2
(45) Date of Patent: Aug. 18, 2015

(54) SUCTION NOZZLE AND ABNORMALITY DETECTION DEVICE THEREFOR

(75) Inventor: Satoru Nishiyama, Chiryu (JP)

(73) Assignee: FUJI MACHINE MFG. CO., LTD., Chiryu-shi (JP)

( * ) Notice: Subject to any disclaimer, the term of this patent is extended or adjusted under 35 U.S.C. 154(b) by 0 days.

(21) Appl. No.: 14/373,116

(22) PCT Filed: Jan. 19, 2012

(86) PCT No.: PCT/JP2012/051110
§ 371 (c)(1),
(2), (4) Date: Jul. 18, 2014

(87) PCT Pub. No.: WO2013/108390
PCT Pub. Date: Jul. 25, 2013

(65) Prior Publication Data
US 2014/0353995 A1 Dec. 4, 2014

(51) Int. Cl.
  *B25J 15/06* (2006.01)
  *G01N 19/00* (2006.01)
  *H05K 13/04* (2006.01)

(52) U.S. Cl.
  CPC ............. *G01N 19/00* (2013.01); *B25J 15/0641* (2013.01); *H05K 13/0413* (2013.01)

(58) Field of Classification Search
  CPC .. B25J 15/0641; G01N 19/00; H05K 13/0413
  USPC ........... 294/183, 185, 186; 414/752.1; 901/40
  See application file for complete search history.

(56) References Cited

U.S. PATENT DOCUMENTS

| | | | | |
|---|---|---|---|---|
| 5,544,411 A | * | 8/1996 | Kano et al. | 29/740 |
| 5,961,169 A | * | 10/1999 | Kalenian et al. | 414/752.1 |
| 6,024,392 A | * | 2/2000 | Blatt | 294/185 |
| 6,328,362 B1 | * | 12/2001 | Isogai et al. | 294/185 |
| 6,431,624 B1 | * | 8/2002 | Dunger | 294/186 |
| 6,851,733 B2 | * | 2/2005 | Mori et al. | 294/186 |

FOREIGN PATENT DOCUMENTS

| | | |
|---|---|---|
| JP | 2006 313838 | 11/2006 |
| JP | 2007 220836 | 8/2007 |
| JP | 2009 088035 | 4/2009 |
| JP | 2009 200204 | 9/2009 |
| JP | 2010 258185 | 11/2010 |
| JP | 2011 029253 | 2/2011 |

OTHER PUBLICATIONS

International Search Report issued Feb. 21, 2012 in PCT/JP12/051110 filed Jan. 19, 2012.

* cited by examiner

*Primary Examiner* — Dean Kramer
(74) *Attorney, Agent, or Firm* — Oblon, McClelland, Maier & Neustadt, L.L.P.

(57) ABSTRACT

An abnormality detection device including an air flow path that is opened and closed by a vertical movement of a nozzle piston in a nozzle holder of a suction nozzle, an air supply path that supplies air to the air flow path, and a flow sensor that detects an amount of air flow in the air supply path. The amount of air flow in the air flow path of the nozzle holder is monitored and based on an output signal from the flow sensor a defect the vertical movement of the nozzle piston is detected.

8 Claims, 3 Drawing Sheets

STATE IN WHICH NOZZLE PISTON IS PUSHED IN

STATE IN WHICH NOZZLE PISTON IS NOT PUSHED IN

STATE IN WHICH NOZZLE PISTON IS PUSHED IN

SUCTION NOZZLE AND ABNORMALITY DETECTION DEVICE THEREFOR

TECHNICAL FIELD

The present disclosure relates to a suction nozzle including a nozzle portion that adsorbs a component and that is vertically movable in a state that the nozzle portion is biased downward by biasing means, and relates to an abnormality detection device for the suction nozzle.

BACKGROUND ART

In a component mounting apparatus, for example, as disclosed in PTL 1 (JP-A-2006-313838) and PTL 2 (JP-A-2009-88035), at the time of adsorbing a component by a suction nozzle or at the time of mounting the adsorbed component on a circuit board, in order to prevent the component from being damaged by an impact, a nozzle portion is provided to a nozzle holder so as to be vertically movable, and the nozzle portion is biased downward by a spring, after the lower end of the nozzle portion comes into contact with the component at the time of a component adsorption operation or after the component adsorbed on the nozzle portion comes into contact with the circuit board at the time of a component mounting operation, the nozzle portion is pushed in against the elastic force of the spring according to the downward movement until the downward movement of a mounting head holding the nozzle holder stops, and thus, the impact on the component can be alleviated.

CITATION LIST

Patent Literature

Patent Literature 1: Japanese Unexamined Patent Application Publication Number 2006-313838
Patent Literature 2: Japanese Unexamined Patent Application Publication Number 2009-88035

SUMMARY OF INVENTION

Problem to be Solved by the Invention

Incidentally, there is a case where the nozzle portion becomes fixed by contaminants jammed in a sliding portion between the nozzle holder and the nozzle portion. However, if the nozzle portion becomes fixed, there is a possibility that erroneous adsorption of the component or erroneous mounting of the component occurs or the impact alleviation effect is not obtained, and thus, the component may be damaged. Therefore, when the nozzle portion becomes fixed, it is necessary to detect such a fixation at an early stage and to stop and check the component mounting apparatus.

Since the component mounting apparatus in the related art has a function of imaging the component adsorbed on the nozzle portion by a camera to monitor the component adsorption posture or the like, in a case where the erroneous adsorption of the component repeatedly occurs due to the fixation of the nozzle portion, the continuously occurring erroneous adsorption of the component is detected by the images imaged by the camera, and then, the operation of the component mounting apparatus stops.

However, in this method of fixation detection, since the component mounting apparatus continues to operate until the continuously occurring erroneous adsorption of the component is detected, it is not possible to detect the fixation of the nozzle portion at an early stage.

Therefore, providing a photoelectric sensor that checks a pushed-in amount of the nozzle portion on the mounting head which holds the suction nozzle can be considered. However, in such a configuration, in order to avoid the collision of the photoelectric sensor and the mounted component at the time of component mounting operation, the photoelectric sensor needs to be disposed at a higher position than the mounted component, and the spring that biases the nozzle portion downward needs to be disposed at a higher position than the photoelectric sensor. Therefore, there is a disadvantage that the size of the suction nozzle increases in the height direction.

Therefore, an object of the present disclosure is to detect the fixation of the nozzle portion at an early stage and to prevent the size of the suction nozzle from increasing in the height direction.

In order to solve the above problems, the present disclosure provides: an abnormality detection device for a suction nozzle in which, to a nozzle holder, a nozzle portion that adsorbs a component is provided so as to be vertically movable and biasing means for downwardly biasing the nozzle portion is provided, and after the lower end of the nozzle portion comes into contact with the component at the time of component adsorption operation or after the component adsorbed on the nozzle portion comes into contact with the circuit board at the time of component mounting operation, the nozzle portion is pushed in against the biasing force of the biasing means according to the downward movement of the nozzle holder. An air flow path that is opened and closed by the vertical movement of the nozzle portion and detection means (a flow sensor or a pressure sensor) for detecting an amount or pressure of air flow flowing in the air flow path are provided to the nozzle holder, and a defect (a fixation) of the vertical movement of the nozzle portion is detected by supplying air to the air flow path and monitoring the amount or pressure of the air flow by the detection means. Here, in the nozzle portion, the vertically moving portion (the nozzle piston) in the nozzle holder and the nozzle tip portion may be separately formed such that both are connected to each other to be integrated, or both may be integrally formed.

In this configuration, if the nozzle portion is not fixed, at the time of component adsorption operation or at the time of component mounting operation, the nozzle portion vertically moves and the air flow path of the nozzle holder is opened and closed. However, if the nozzle portion is fixed and does not vertically move, since the air flow path is not opened and closed, there is no change in the amount and the pressure of air flow flowing in the air flow path. From this relationship, if the amount and the pressure of the air flow flowing in the air flow path are monitored by the detection means, the defect (fixation) of the vertical movement of the nozzle portion can be detected at an early stage. Moreover, since a photoelectric sensor that checks a pushed-in amount of the nozzle portion is not provided, it is possible to dispose the biasing means that biases the nozzle portion downward at a position of optimized height, and thus, it is possible to prevent the size of the suction nozzle from increasing in the height direction.

In this case, the nozzle holder may be detachably attached to a mounting head which moves in X, Y, and Z directions of a component mounting apparatus, an air supply path that supplies air to the air flow path of the nozzle holder may be provided to the mounting head, and the detection means may be mounted on the mounting head so as to detect the amount or pressure of the air flow flowing in the air supply path of the mounting head. In short, since the amount of air flow flowing in the air flow path of the nozzle holder is the same as the amount of the air flow flowing in the air supply path of the mounting head, the amount or the pressure of the air flow flowing in the air supply path of the mounting head is detected as the information of the amount or pressure of the air flow flowing in the air flow path of the nozzle holder. In this way, since the detection means (the flow sensor or the pressure sensor) can be mounted on the mounting head, there is no need to provide the detection means on the suction nozzle, and thus, it is possible to prevent the structure of the suction nozzle being complicated.

Specifically, in an inner peripheral surface of the nozzle holder, a hole of the air flow path and an atmosphere communication hole may be formed. At the vertically moving portion of the nozzle portion in the nozzle holder, a cylindrical valve body that opens and closes the hole of the air flow path and the atmosphere communication hole may be fitted therein. At the outer peripheral portion of the cylindrical valve body, a communication groove that causes the hole of the air flow path and the atmosphere communication hole to communicate with each other may be formed when the pushed-in amount of the nozzle portion is a predetermined value. Here, the predetermined value may be appropriately set within the range of vertical stroke of the nozzle portion or may be a lower limit value of the vertical stroke (pushed-in amount is zero). In the present invention, the cylindrical valve body may be integrally formed in the nozzle portion.

BRIEF DESCRIPTION OF DRAWINGS

FIG. 2 is a longitudinal sectional view illustrating a state of the suction nozzle when the nozzle piston is pushed in.

DESCRIPTION OF EMBODIMENTS

Figure 1:
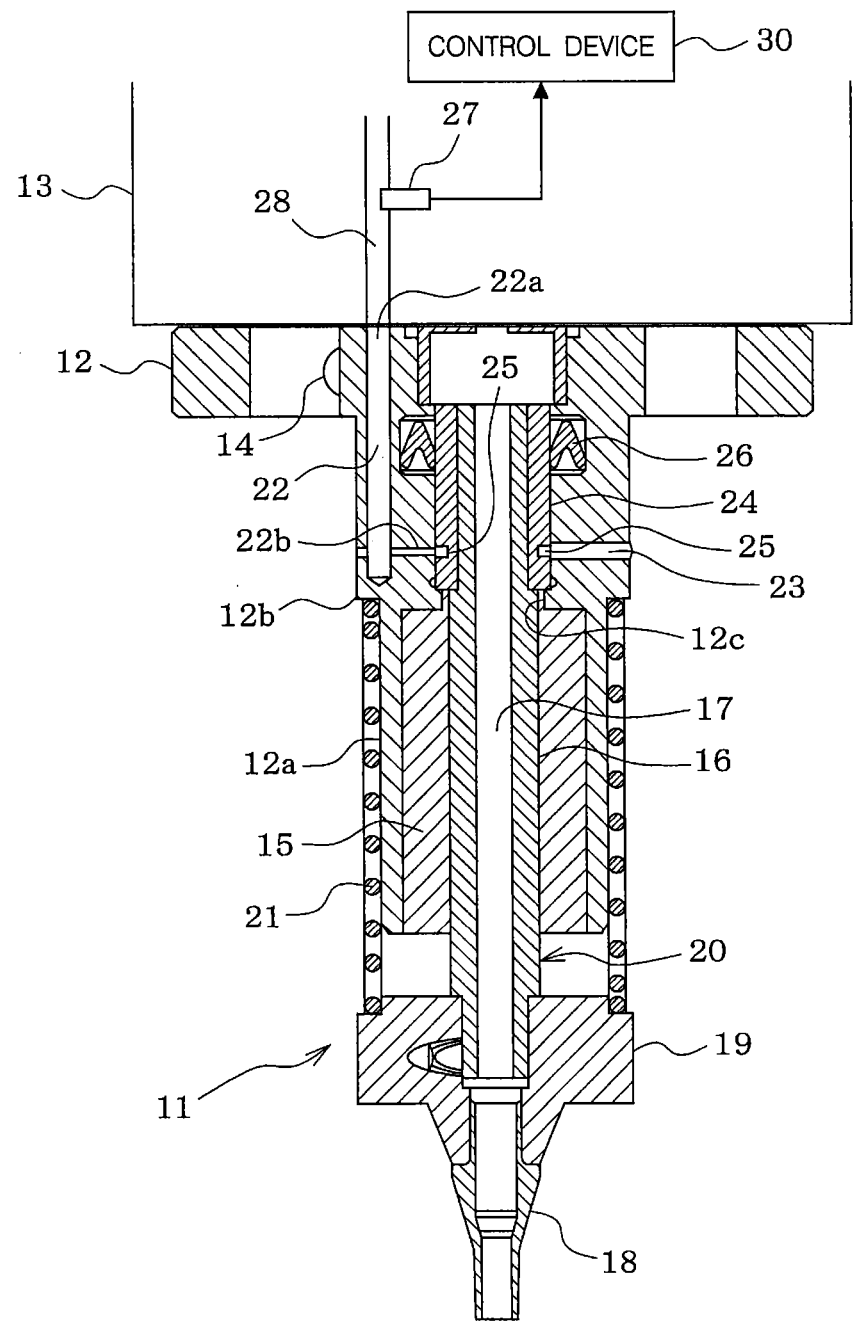
FIG. 1 is a longitudinal sectional view illustrating a state of a suction nozzle when a nozzle piston is not pushed in, in the first embodiment of the present invention.

Hereinafter, a detailed embodiment of the present invention will be described.

First, a configuration of a suction nozzle 11 will be described based on FIG. 1.

A nozzle holder 12 of the suction nozzle 11 is detachably attached to a mounting head 13 which moves in X, Y, and Z directions of a component mounting apparatus. Any type of method of attaching and detaching of the suction nozzle 11 may be used, for example, the suction nozzle 11 may be held by hooking an engaging member (not illustrated) provided on the mounting head 13 onto a pin 14 provided on the nozzle holder 12, or the suction nozzle 11 may be held to the mounting head 13 by a negative pressure (vacuum pressure).

In the inner peripheral portion of a cylindrical portion 12a which extends downward from the nozzle holder 12, a cylindrical support member 15 is fitted and fixed by press-fitting or the like, and in the inner peripheral portion of the cylindrical support member 15, a nozzle piston 16 is inserted and supported so as to be vertically movable. In the nozzle piston 16, a negative pressure introduction passage 17 which introduces the negative pressure supplied from a mounting head 13 side is formed so as to penetrate in the vertical direction, and at the lower end portion of the nozzle piston 16, a nozzle tip portion 18 that adsorbs the component by the negative pressure introduced from the negative pressure introduction passage 17 is coaxially fixed by a connection member 19. In this case, the nozzle piston 16 and the nozzle tip portion 18 are connected by the connection member 19, and thus, the nozzle portion 20 is configured.

Regarding the fixing of the nozzle tip portion 18 and the connection member 19, the nozzle tip portion 18 is fixed to the connection member 19 by tightening a male screw portion formed on the upper portion of the nozzle tip portion 18 to the female screw portion of the connection member 19, and regarding the fixing of the connection member 19 and the nozzle piston 16, the connection member 19 is fixed to the lower end portion of the nozzle piston 16 by tightening a screw (not illustrated) to the connection member 19 which is fitted into the lower end portion of the nozzle piston 16 thereof in the radial direction from the outer peripheral side, and making the tip of the screw be in pressure contact against the outer peripheral surface of the nozzle piston 16. In this way, in a case where the type of nozzle is changed, such as changing an opening diameter of the nozzle tip portion 18, the nozzle tip portion 18 and the connection member 19 are removed from the nozzle piston 16 by loosening the screw which fixes the connection member 19 to the nozzle piston 16, and then another nozzle tip portion 18 and connection member 19 are substituted to be fixed to the nozzle piston 16.

The connection member 19 is positioned at a lower portion than the lower end of the cylindrical portion 12a of the nozzle holder 12, and a gap for allowing the vertical movement of the nozzle portion 20 between the connection member 19 and the lower end of the cylindrical portion 12a of the nozzle holder 12 is secured. The outer diameter of the connection member 19 is formed so as to be slightly larger than the outer diameter of a spring 21 (biasing means) mounted on the outer peripheral portion of the cylindrical portion 12a of the nozzle holder 12, and the spring 21 is compressed and inserted between the connection member 19 and an upper end step portion 12b of the cylindrical portion 12a of the nozzle holder 12, and thus, the nozzle portion 20 is biased downward by the elastic force of the spring 21. In this configuration, at the time of the component adsorption operation, after the lower end of the nozzle tip portion 18 comes into contact with the component or at the time of the component mounting operation, after the component adsorbed on the nozzle tip portion 18 comes into contact with the circuit board, the nozzle portion 20 is pushed in against the elastic force of the spring 21 according to the downward movement until the downward movement of the mounting head 13 holding the nozzle holder 12 stops.

An air flow path 22 is formed in the nozzle holder 12, and a hole on the inlet side 22a of the air flow path 22 extends through the upper surface of the nozzle holder 12 and a hole on the outlet side 22b extends through the inner peripheral surface of the nozzle holder 12. Furthermore, in the nozzle holder 12, an atmosphere communication hole 23 is formed so as to extend through the inner and outer peripheral surfaces of the nozzle holder 12 at the position with the same height as that of the hole on the outlet side 22b of the air flow path 22.

At the upper portion of the nozzle piston 16, the hole 22b of the air flow path 22 of the nozzle holder 12 and a cylindrical valve body 24 that opens and closes the atmosphere communication hole 23 are fitted and fixed by press-fitting, or the like. At the outer peripheral portion of the cylindrical valve body 24, an annular communication groove 25 is formed, and when the pushed-in amount of the nozzle piston 16 with respect to the nozzle holder 12 is a predetermined value (within a predetermined range), the communication groove 25 is matched to the hole 22b of the air flow path 22 and to the atmosphere communication hole 23, and thus, the hole 22b of the air flow path 22 and the atmosphere communication hole 23 are brought into a communicating state by the communication groove 25, and when the pushed-in amount of the nozzle piston 16 with respect to the nozzle holder 12 is other than the predetermined value (out of the predetermined range), the hole 22b of the air flow path 22 and the atmosphere communication hole 23 are brought into a closed state by the cylindrical valve body 24.

Figure 2:
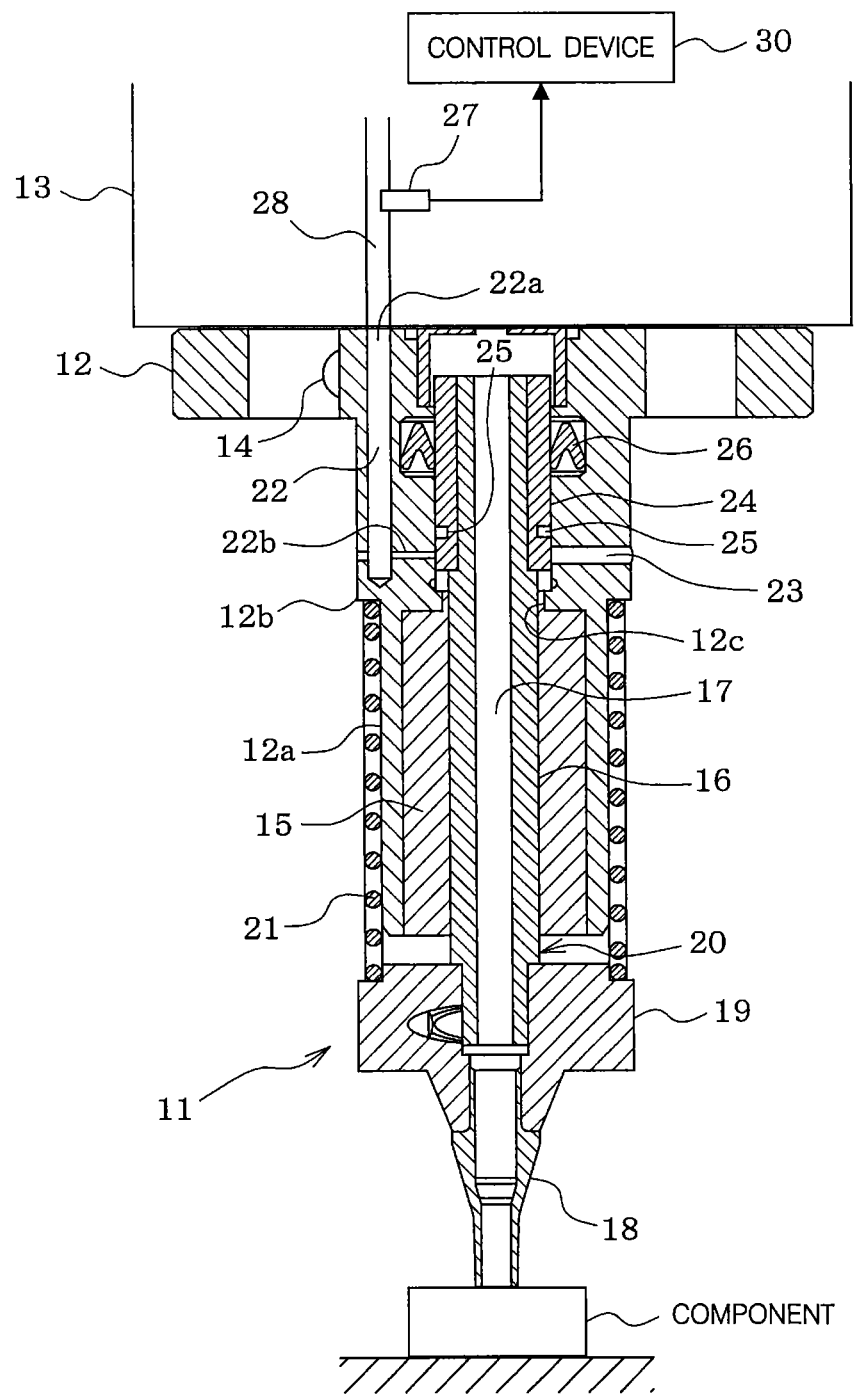

In the present embodiment, as illustrated in FIG. 1, when the nozzle piston 16 is positioned at the lowest position of the vertical stroke (the pushed-in amount of the nozzle piston 16 is zero) thereof, the hole 22b of the air flow path 22 and the atmosphere communication hole 23 are brought into the communicating state by the communication groove 25, and as illustrated in FIG. 2, when the nozzle piston 16 is pushed in, the hole 22b of the air flow path 22 and the atmosphere communication hole 23 are brought into a closed state by the cylindrical valve body 24.

At the lower end of the region where the cylindrical valve body 24 slides in the inner peripheral portion of the nozzle holder 12, a ring shaped stopper portion 12c is formed so as to protrude to the inner peripheral side, and thus, the position where the lower end of the cylindrical valve body 24 contacts the stopper portion 12c becomes the lowest position (the pushed-in amount is zero) of the vertical stroke of the nozzle piston 16. At the region where the cylindrical valve body 24 slides in the inner peripheral portion of the nozzle holder 12, a packing 26 is mounted in order to prevent the negative pressure from leaking from the gap between the inner peripheral surface of the nozzle holder 12 and the outer peripheral surface of the cylindrical valve body 24.

In the mounting head 13 that holds the nozzle holder 12 of the suction nozzle 11 configured as described above, a negative pressure supply path (not illustrated) that supplies the negative pressure to the negative pressure introduction passage 17 of the nozzle piston 16, and the air supply path 28 that supplies air to the air flow path 22 of the nozzle holder 12. Furthermore, in the mounting head 13, a flow sensor 27 (detection means) that detects the amount of air flow flowing in an air supply path 28 of the mounting head 13 is provided. The output signal of the flow sensor 27 is read into the control device 30 of the component mounting apparatus such that the amount of air flow flowing in the air flow path 22 of the nozzle holder 12 from the air supply path 28 of the mounting head 13 is monitored.

Incidentally, there is a case where the nozzle piston 16 is fixed by contaminants jammed in a sliding portion between the nozzle holder 12 and the nozzle piston 16. However, if the nozzle piston 16 is fixed, there is a possibility that erroneous adsorption of the component or erroneous mounting of the component occurs or the impact alleviation effect is not obtained, and thus, the component may be damaged. Therefore, when the nozzle piston 16 is fixed, it is necessary to detect such a fixation at an early stage and to stop and check the component mounting apparatus.

Figure 3:
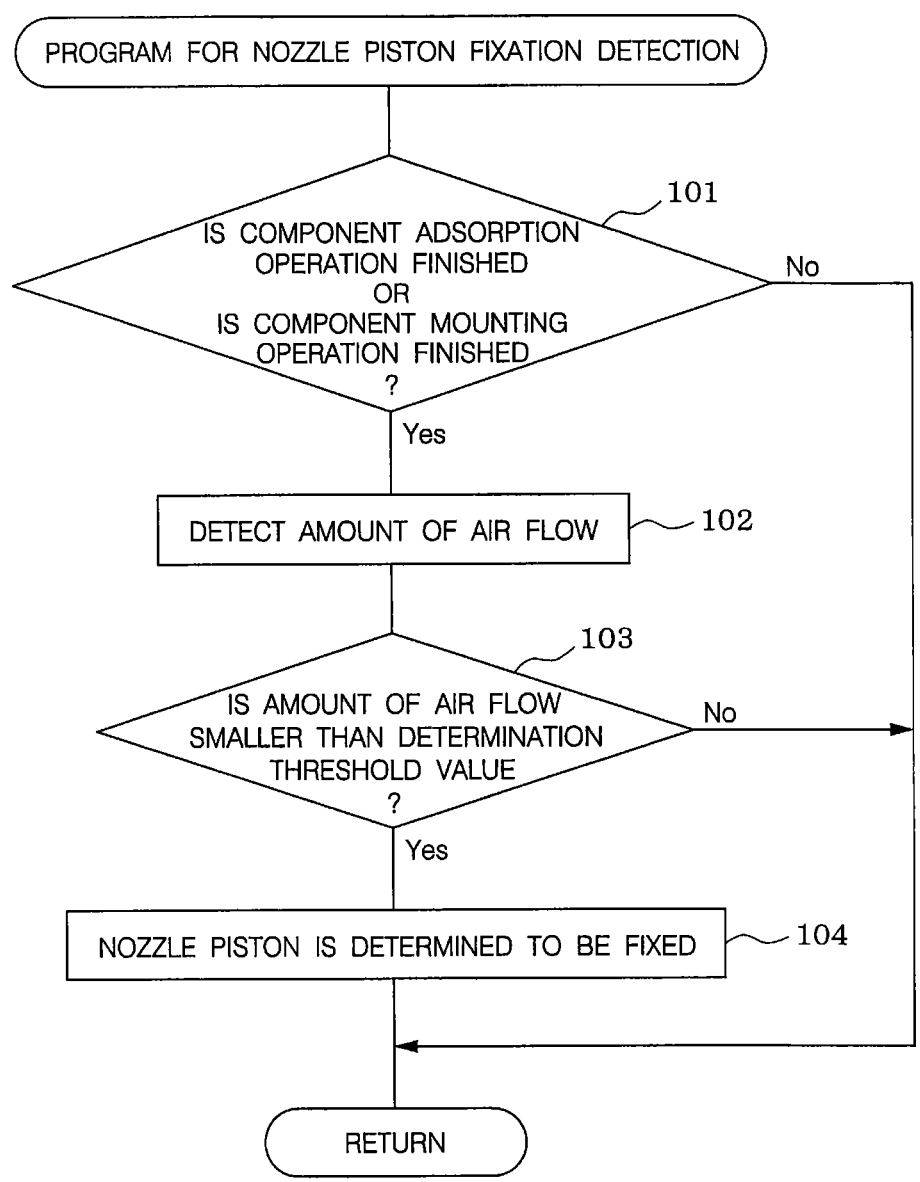
FIG. 3 is a flow chart illustrating a processing flow of a nozzle piston fixation detection program.

Here, the control device 30 of the component mounting apparatus monitors the amount of air flow flowing in the air flow path 22 of the nozzle holder 12 based on the output signal of the flow sensor 27 by repeatedly executing a nozzle piston fixation detection program illustrated in FIG. 3 in a predetermined period, and then, detects the defect (fixation) of the vertical movement of the nozzle piston 16. In short, if the nozzle piston 16 is not fixed, at the time of the component adsorption operation or at the time of the component mounting operation, the nozzle piston 16 vertically moves and the air flow path 22 of the nozzle holder 12 is opened and closed by the cylindrical valve body 24 of the nozzle piston 16. However, if the nozzle piston 16 is fixed and does not vertically move, since the air flow path 22 is not opened and closed, there is no change in the amount of air flow flowing in the air flow path 22. From this relationship, if the amount of air flow flowing in the air flow path 22 is monitored by the flow sensor 27, the defect (fixation) of the vertical movement of the nozzle piston 16 can be detected at an early stage.

Incidentally, even though the nozzle piston 16 is fixed at the lowest position of the vertical stroke thereof (the pushed-in amount of the nozzle piston 16 is zero), in many cases, the nozzle piston 16 is pushed in by the component adsorption operation or the component mounting operation. However, if the nozzle piston 16 is fixed in the state of being pushed-in, the nozzle piston 16 does not return to the lowest position (the pushed-in amount of the nozzle piston 16 is zero) of the vertical stroke thereof, which causes the erroneous adsorption of the component or the erroneous component mounting. The nozzle piston fixation detection program in FIG. 3 is a program that detects the fixed state of the nozzle piston 16 in a state of being pushed-in.

Hereinafter, the processing of a nozzle piston fixation detection program in FIG. 3 will be described. The program is executed in a predetermined period during the operation of the component mounting apparatus. When the program is started, firstly, it is determined in STEP 101 whether the component adsorption operation is finished or the component mounting operation is finished. Since the nozzle piston 16 is pushed in against the elastic force of the spring 21 by the component adsorption operation or the component mounting operation, each time the pushing-in operation of the nozzle piston 16 is finished and the suction nozzle 11 goes up is the timing for determining the presence or absence of the fixation of the nozzle piston 16.

When the determination in STEP 101 is "No", the process determines that it is not the timing for determining the fixation of the nozzle piston, and ends the program without executing the processing thereafter. However, when the determination in STEP 101 is "Yes", the process determines that it is the timing for determining the fixation of the nozzle piston, proceeds to STEP 102 to read the output signal of the flow sensor 27, and detects the amount of air flow flowing in the air flow path 22 of the nozzle holder 12 from the air supply path 28 of the mounting head 13.

Then, the process proceeds to STEP 103, whether or not the amount of air flow detected by the flow sensor 27 is smaller than a determination threshold value is determined. In a case where the nozzle piston 16 is not fixed, if the pushing-in operation of the nozzle piston 16 is finished and the suction nozzle 11 goes up, as illustrated in FIG. 1, since the nozzle piston 16 is pushed down to the lowest position of the vertical stroke of the nozzle piston 16 by the elastic force of the spring 21, the hole 22b of the air flow path 22 and the atmosphere communication hole 23 are brought into the communication state by the communication groove 25 of the cylindrical valve body 24 of the nozzle piston 16, and the amount of air flow flowing in the air flow path 22 increases. However, if the nozzle piston 16 is fixed during the pushing-in operation thereof, even if the pushing-in operation is finished and the suction nozzle 11 goes up, since the nozzle piston 16 does not return to the lowest position of the vertical stroke of the nozzle piston 16, the hole 22b of the air flow path 22 remains being in the closed state due to the cylindrical valve body 24 of the nozzle piston 16, and thus, the amount of air flow flowing in the air flow path 22 does not increase.

From this relationship, in STEP 103, whether or not the amount of air flow flowing in the air flow path 22 is smaller than the determination threshold value is determined, and if the amount of air flow is smaller than the determination threshold value, the nozzle piston 16 is determined not to have returned to the lowest position of the vertical stroke thereof, the process proceeds to STEP 104, and the nozzle piston 16 is determined to be fixed, and if the amount of air flow is equal to or larger than the determination threshold value, since the nozzle piston 16 does not return to the lowest position of the vertical stroke thereof, the nozzle piston 16 is determined not to be fixed, and the program ends as it is.

In a case where the nozzle piston 16 is completely fixed at the lowest position of the vertical stroke thereof and the state in which the nozzle piston 16 is no longer pushed in at all is detected even at the time of component adsorption operation or the component mounting operation, for example, at the time of component adsorption operation or the component mounting operation, when the downward movement of the mounting head 13 is stopped (that is, if the nozzle piston 16 is not fixed, when the amount of pushing-in of the nozzle holder 12 becomes a maximum), whether or not the amount of air flow detected by the flow sensor 27 is determined to be larger than the determination threshold value, if the amount of air flow is larger than the determination threshold value, then, the nozzle piston 16 is determined to be fixed at the lowest position of the vertical stroke thereof, and if the amount of air flow is smaller than the determination threshold value, since the nozzle piston 16 is pushed in and the air flow path 22 of the nozzle holder 12 is closed by the cylindrical valve body 24 of the nozzle piston 16, the nozzle piston 16 may be determined not to be fixed.

Alternatively, during the component adsorption operation or the component mounting operation, whether or not the absolute value of the changed amount of the amount of air flow detected by the flow sensor 27 is equal to or larger than the determination threshold value is monitored, if the absolute value of the changed amount of the amount of air flow is equal to or larger than the determination threshold value, the nozzle piston 16 is determined to be pushed in and the air flow path 22 of the nozzle holder 12 is determined to be opened and closed, and thus, the nozzle piston 16 is determined not to be fixed, and if the absolute value of the changed amount of the amount of air flow is smaller than the determination threshold value, the air flow path 22 of the nozzle holder 12 may be determined not to be opened and closed, and thus, the nozzle piston 16 may be determined to be fixed.

In the present embodiment described above, since a valve structure is configured using the slide portion of the nozzle holder 12 and the nozzle piston 16, and the amount of air flow flowing in the air flow path 22 which is opened and closed by the vertical movement of the nozzle piston 16 is monitored by the flow sensor 27, it is possible to detect the fixation of the nozzle piston 16 at an early stage. Moreover, since a photoelectric sensor that checks the amount of pushing-in of the nozzle piston 16 is not provided, it is possible to dispose the spring 21 that biases the nozzle piston 16 downward at a position of optimized height, and thus, it is possible to prevent the size of the suction nozzle 11 from increasing in the height direction. Furthermore, since the flow sensor 27 is mounted on the mounting head 13, there is no need to provide the flow sensor 27 on the suction nozzle 11, and thus, it is possible to prevent the structure of the suction nozzle 11 being complicated.

In the present embodiment, the amount of air flow flowing in the air flow path 22 (the air supply path 28 of the mounting head 13) of the nozzle piston 16 is monitored by the flow sensor 27 and then, the opening and closing of the air flow path 22 is detected. However, the opening and closing of the air flow path 22 may be detected by monitoring a pressure in the air flow path 22 (the air supply path 28 of the mounting head 13) of the nozzle piston 16 by a pressure sensor. In this case, when the air flow path 22 is opened, the pressure detected by the pressure sensor is the atmospheric pressure, and when the air flow path 22 is closed, since the pressure detected by the pressure sensor increases or decreases than the atmospheric pressure according to the pressure (positive or negative pressure) supplied to the air flow path 22, similar to the case of the amount of the air flow, even though the pressure is detected, it is possible to detect the opening and closing of the air flow path 22.

In addition, in the present embodiment, the vertically moving portion (the nozzle piston 16) of the nozzle portion 20 in the nozzle holder 12 and the nozzle tip portion 18 are separately formed and both are connected and integrated by the connection member 19, however, both may be integrally formed.

In the present embodiment, the cylindrical valve body 24 is fitted and fixed to the nozzle piston 16, but both may be integrally formed.

In addition, in the present embodiment, when the nozzle piston 16 is positioned at the lowest position of the vertical stroke thereof (when the pushed-in amount of the nozzle piston 16 is zero), the hole 22b of the air flow path 22 and the atmosphere communication hole 23 are in the state of communication due to the communication groove 25. However, when the pushed-in amount of the nozzle piston 16 is a predetermined value (positive value), the hole 22b of the air flow path 22 and the atmosphere communication hole 23 may be in the state of communication due to the communication groove 25, and the position where the opening and closing of the air flow path 22 is switched may be appropriately set within the range of vertical stroke of the nozzle piston 16.

Additionally, it is needless to say that the present invention can be variously modified within the scope not departing from the spirit of the invention, for example, the position of the valve structure configured using the slide portion of the nozzle holder 12 and the nozzle piston 16, or the configuration thereof may be appropriately changed.

REFERENCE SIGNS LIST

11 suction nozzle
12 nozzle holder
13 mounting head
15 cylindrical support member
16 nozzle piston
17 negative pressure introduction passage
18 nozzle tip portion
19 connection member
20 nozzle portion
21 spring (biasing means)
22 air flow path
22a hole on the inlet side
22b hole on the outlet side
23 atmosphere communication hole
24 cylindrical valve body
25 communication groove
27 flow sensor (detection means)
28 air supply path
30 control device

The invention claimed is:

1. An abnormality detection device for a suction nozzle including a nozzle holder, a nozzle portion that adsorbs a component, the nozzle portion being vertically movable, and biasing means for biasing downward the nozzle portion, the abnormality detection device comprising:

an air flow path in the nozzle holder that is opened and closed by vertical movement of the nozzle portion; and detection means for detecting an amount or a pressure of air flow in the air flow path are provided to the nozzle holder, and wherein a defect of the vertical movement of the nozzle portion is detected by supplying air to the air flow path and monitoring the amount or pressure of the air flow by the detection means.

2. The abnormality detection device for a suction nozzle according to claim 1, wherein the nozzle holder is detachably attached to a mounting head which moves in X, Y, and Z directions of a component mounting apparatus, wherein an air supply path in the mounting head supplies air to the air flow path of the nozzle holder, and wherein the detection means is mounted on the mounting head so as to detect the amount or the pressure of the air flow flowing in the air supply path of the mounting head.

3. The abnormality detection device for a suction nozzle according to claim 2, wherein a hole of the air flow path and an atmosphere communication hole are each formed in an inner peripheral surface of the nozzle holder, wherein a cylindrical valve body that opens and closes the hole of the air flow path and the atmosphere communication hole is fitted in the inner peripheral surface of the nozzle holder, and wherein a communication groove, that causes the hole of the air flow path and the atmosphere communication hole to communicate with each other in response to a pushed-in amount of the nozzle portion is a predetermined value, is formed at the outer peripheral portion of the cylindrical valve body.

4. The abnormality detection device for a suction nozzle according to claim 1, wherein a hole of the air flow path and an atmosphere communication hole are each formed in an inner peripheral surface of the nozzle holder, wherein a cylindrical valve body that opens and closes the hole of the air flow path and the atmosphere communication hole is fitted in the inner peripheral surface of the nozzle holder, and wherein a communication groove, that causes the hole of the air flow path and the atmosphere communication hole to communicate with each other in response to a pushed-in amount of the nozzle portion is a predetermined value, is formed at the outer peripheral portion of the cylindrical valve body.

5. A suction nozzle, comprising:
a nozzle holder,
a nozzle portion including a negative pressure passage that adsorbs a component, the nozzle portion being vertically movable, and
biasing means for downwardly biasing the nozzle portion
wherein after a lower end of the nozzle portion comes into contact with the component at a time of a component adsorption operation or after the component adsorbed on the nozzle portion comes into contact with a circuit board at a time of a component mounting operation, the nozzle portion is pushed in against a biasing force of the biasing means until the downward movement of the nozzle holder stops, and wherein an air flow path, that is opened and closed by the vertical movement of the nozzle portion, is provided to the nozzle holder independently and separately from the negative pressure passage.

6. The suction nozzle according to claim 5, wherein a hole of the air flow path and an atmosphere communication hole are each formed in an inner peripheral surface of the nozzle holder, and wherein a communication groove is formed at an outer peripheral portion of the cylindrical valve body to cause the hole of the air flow path and the atmosphere communication hole to communicate with each other.

7. An abnormality detection device for a suction nozzle including a nozzle holder, a nozzle portion that adsorbs a component, the nozzle portion being vertically movable, and a spring to bias downward the nozzle portion, the abnormality detection device comprising:

an air flow path in the nozzle holder that is opened and closed by vertical movement of the nozzle portion; and a sensor that detects an amount or a pressure of air flow in the air flow path are provided to the nozzle holder, and wherein a defect of the vertical movement of the nozzle portion is detected by supplying air to the air flow path and monitoring the amount or pressure of the air flow by the sensor.

8. A suction nozzle, comprising:
a nozzle holder,
a nozzle portion including a negative pressure passage that adsorbs a component, the nozzle portion being vertically movable, and
a spring to downwardly bias the nozzle portion
wherein after a lower end of the nozzle portion comes into contact with the component at a time of a component adsorption operation or after the component adsorbed on the nozzle portion comes into contact with a circuit board at a time of a component mounting operation, the nozzle portion is pushed in against a biasing force of the spring until the downward movement of the nozzle holder stops, and wherein an air flow path, that is opened and closed by the vertical movement of the nozzle portion, is provided to the nozzle holder independently and separately from the negative pressure passage.

* * * * *